United States Patent
Martin

(10) Patent No.: US 8,088,341 B2
(45) Date of Patent: Jan. 3, 2012

(54) ANALYTE COLLECTION DEVICES AND METHODS

(75) Inventor: Michael Martin, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 1116 days.

(21) Appl. No.: 11/881,333

(22) Filed: Jul. 25, 2007

(65) Prior Publication Data

US 2009/0028208 A1 Jan. 29, 2009

(51) Int. Cl.
*B01L 99/00* (2010.01)

(52) U.S. Cl. ............... 422/500; 422/107; 219/200

(58) Field of Classification Search ............ 422/420, 422/500, 109; 219/200; 2/420, 500, 109
See application file for complete search history.

(56) References Cited

U.S. PATENT DOCUMENTS

| | | | |
|---|---|---|---|
| 3,768,300 A | 10/1973 | Nemeth | |
| 4,935,040 A | 6/1990 | Goedert | |
| 5,690,763 A | 11/1997 | Ashmead et al. | |
| 5,707,502 A | 1/1998 | McCaffrey et al. | |
| 5,720,798 A | 2/1998 | Nickerson et al. | |
| 5,817,012 A | 10/1998 | Schoendorfer | |
| 5,970,803 A | 10/1999 | Staples et al. | |
| 6,171,378 B1 | 1/2001 | Manginell et al. | |
| 6,242,195 B1 | 6/2001 | Idusogie et al. | |
| 6,442,997 B1 | 9/2002 | Megerle et al. | |
| 6,527,835 B1 | 3/2003 | Manginell et al. | |
| 6,666,907 B1 | 12/2003 | Manginell et al. | |
| 0,095,722 A1 | 5/2005 | McGill et al. | |
| 6,893,879 B2 | 5/2005 | Petersen et al. | |
| 0,226,778 A1 | 10/2005 | Houser | |
| 6,989,891 B2 | 1/2006 | Braig et al. | |
| 7,306,649 B2 | 12/2007 | Boyle et al. | |

OTHER PUBLICATIONS

Hughes et al., "A MEMS Based Hybrid Preconcentrator/Chemiresistor Chemical Sensor," Sep. 1, 2002.
Micro Analytical Systems Department Technology—μChemLab™ Face Sheet, Sandia Corporation, Dec. 30, 2002.
R.A. McGill, M.H. Abraham, J.W. Grate, "Choosing Polymer Coatings for Chemical Sensors," Chemtech, Sep. 1994, pp. 27-37.

*Primary Examiner* — Jill Warden
*Assistant Examiner* — Monique Cole
(74) *Attorney, Agent, or Firm* — Stoll Keenon Ogden PLLC; Stephen C. Hall; Justin M. Tromp

(57) ABSTRACT

An aspect of the invention is directed to an analyte collection device of the type that includes at least one plate for storing the analyte and a heating element for heating the at least one plate. An example device comprises a controller linked to the heating element that heats the at least one plate to a first temperature, takes a measurement of a property of the at least one plate, and uses the measurement to estimate one or more of the amount of the analyte on the plate and the amount of contaminant on the plate.

20 Claims, 4 Drawing Sheets

ANALYTE COLLECTION DEVICES AND METHODS

STATEMENT OF GOVERNMENT INTEREST

This invention was made with Government assistance under NRL Grant No. N00173-02-2-C002. The Government has certain rights in this invention.

FIELD OF THE INVENTION

A field of the invention is analyte collection. The invention is useful, for example, in analyte detection and analysis systems and methods, as might be used for the collection, detection and analysis of a wide range of vapors or gases, particulate and liquid bound analytes. Another field of the invention is analyte storage and delivery. The invention is useful, for example, to store and deliver hazardous materials, including explosive related materials, toxic industrial chemicals (TICS) or chemical or biological agents or toxins in a controlled manner. Another field of the invention is methods, systems and program products for operating analyte collection devices.

BACKGROUND OF THE INVENTION

In many analytical systems, discovering the nature of an unknown substance normally requires the substance to first be collected. There are detector systems that analyze a fluid flow analyte stream, i.e., vapors or gases, particulates and liquid bound analytes. Some detector systems are based, for example, on an optical analysis that determines analyte characteristics by subjecting a quantity of the analyte to a light beam and measuring the scattering or fluorescence effects. Chromatography detector systems, for example, are sometimes based upon the optical effects produced by analyte samples. Other detector systems utilize chemical analysis, thermal properties, and the like. There are both quantitative and qualitative analysis detector systems.

Before a sample may be analyzed by chromatography or by many other types of analytical techniques, the sample must be collected and then delivered to a detector system. Many samples of interest are available outside of a controlled setting or are present in such low concentrations that special emphasis must be placed on sample collection, with an example being safety testing of environments that humans occupy. There is a recently heightened awareness of the potential for the intentional detonation of explosives or release of chemical or biological agents into environments occupied by humans. The environments might include open or enclosed spaces in work environments, public environments, or military environments, etc. Many building environments with ducted HVAC (heating ventilation and air conditioning) have the potential for the intentional release of TICS or chemical and biological agents into closed or open spaces occupied by military or civilian personnel. Manufacturing operations also have the potential to permit the escape of hazardous chemicals or biological agents into a manufacturing environment or to an external environment surrounding a manufacturing plant.

In some situations, detection may be desirable in a matter of seconds, but in others, an extended period of time may be used for collection before performing an analysis. An example of the latter case involves workers that may be exposed over a time period to unacceptable levels of harmful agents. Another example of the latter case is when cargo containers are transported from country to country by sea, it may be desirable to collect a sample over a period of several days prior to analysis.

In both uncontrolled settings and controlled settings, analytical resolution and the sensitivity of detection is dependent upon the efficiency of analyte collection and the efficacy of delivery of collected analyte to a detection system. It is desirable, for example, to detect very low levels of toxic or hazardous materials in a particular environment. Gas chromatography and other analytical techniques can employ a variety of detector types, and have been demonstrated to be very sensitive types of analysis techniques, for example. Another example is a chemresistor based device, which uses a detector whose resistivity changes when it is exposed to particular chemical vapors. Whatever the type of detector system, however, concentrating analyte in a stage prior to the detector system can improve detection limits for the analyte(s) of interest, and can also provide a more reliable quantitative or qualitative determination of an analyte.

Others have worked on concentrating analytes, and have proposed systems including a micro scale collection device. A group working at Sandia National Laboratory in Albuquerque, N. Mex. has developed chemical preconcentrators including a preconcentrator heated plate that incorporates a sorbent material coating. This work is discussed, for example, in Manginell et al. U.S. Pat. No. 6,257,835, entitled Chemical Preconcentrator with Integral Thermal Flow Sensor and in Manginell et al. U.S. Pat. No. 6,171,378, entitled Chemical Preconcentrator, which are incorporated herein by reference. The chemical preconcentrator used in that work is formed from a substrate having a suspended membrane, such as low-stress silicon nitride. A resistive heating element is deposited over the membrane and coated with a sorbent, such as a hydrophobic sol-gel coating or a polymer coating. A fluid flow is passed over the sorbent to achieve a collection. A high concentration may then be delivered to a detector system by desorbing, which is achieved by heating the resistive heating element.

One advantage of this work by Manginell and others is that it can provide a relatively high concentration of analyte by collecting it over a long period, and then delivering it in a short amount of time. Another advantage is the MEMS (microelectromechanical systems) micro scale of the device and the MEMS fabrication techniques that permit integration of the device with other system components, for example to form a micro analytical system.

In another style of analyte collector, a column that is packed with a porous adsorbent is used to collect analyte by flowing air through the column and thermally desorbing collected material. The pressure drop associated with this sort of device is typically too high for high flow applications and requires higher power consumption. If the amount of adsorbent is minimized to allow higher flows or faster desorption, the dynamic range is compromised.

However, known prior devices have some drawbacks associated with them. With embodiments of the present invention, some or all of these drawbacks are overcome. Some problems in the art relate to the difficulty of determining the quantity of material collected in a collection device prior to delivery to a detector. In order to perform many chemical analysis (and other types) of tests, a minimum and/or an optimal amount of sample is called for. Measurement of the quantity of material available for delivery to a detector is useful for determination the presence of a sufficient or optimal amount of analyte. If a sufficient and/or optimal amount has been collected, further collection is not necessary.

With many prior art collection and preconcentrator systems, determining the amount of analyte collected is difficult or even impossible. A direct measurement of mass can potentially be used in some applications (e.g., compare device mass before and after collection). In many applications, however, the relatively minuscule mass of analyte collected when compared to the mass of the device make this an unattractive and impractical option.

Another unresolved problem in the art relates to the ability to detect non-volatile and other contaminants that accumulate over time on the sorbent. Dust and other non-volatile particulate may contaminate the sorbent over time and begin to lower collection efficiency of the sorbent as its active sites are affected by the contaminants. Determining when contaminants are present and in what quantity, however, is difficult. Because of this difficulty, systems of the prior art are often scheduled for cleaning and removal of contaminants on an arbitrary schedule that risks cleaning the devices too frequently or not frequently enough. Inefficiencies therefore result.

SUMMARY OF THE INVENTION

An aspect of the invention is directed to a method for operating an analyte collection device of the type that includes at least one plate for storing analyte. An example method comprises the steps of heating the at least one plate to a first temperature, taking a measurement of a property of the at least one plate at one or more of during the step of heating the at least one plate and after the at least one plate has been heated to the first temperature, and using the measurement to estimate one or more of the amount of the analyte on the plate and the amount of contaminant on the plate. In some embodiments of the invention, steps of measuring changes in the thermal time constant or thermal conductivity of the plate can be indicative of collected material.

Another example system of the invention is directed to an analyte collection device comprising one or more preconcentrators such as plates which may be (but are not necessarily) on a micro-scale. The plates optionally may include a sorbent coating on at least a portion of them. A heating element for heating the one or more micro scale plates is also provided. A controller is linked to the heating element and configured to heat the one or more plates to a first temperature and to measure one or more properties of the plate and to use the one or more properties to estimate the quantity of analyte collected on the sorbent coating. The controller is further configured to heat the micro scale plate to at least a second temperature that is greater than the first temperature to cause the analyte to be released from the sorbent.

Another embodiment of the invention is directed to a computer program product including computer readable instructions stored on a memory medium, the program product for use with a collector device of the type that includes at least one plate with sorbent thereon for collecting analyte, the analyte released when the collector device heats the plate to a desorbing temperature. The program instructions when executed by one or more computers are useful to cause the collector device to be heated to an elevated temperature that is substantially below the desorbing temperature, to measure a property of the plate, and to use the measured property to determine whether sufficient analyte has been collected to proceed with testing.

DETAILED DESCRIPTION OF THE EXAMPLE EMBODIMENTS

Before discussing example embodiments of the invention in detail, it will be appreciated that the present invention may be practiced in the form of one or more of a method, a system or a program product. It will further be appreciated that description herein of one embodiment of the invention may likewise be useful to illustrate a different embodiment. By way of example, a method of the invention may include steps of using a system of the invention. A program product of the invention may comprise program instructions useful for carrying out a method of the invention and/or for operating a system of the invention. Accordingly, description of a method, system or program product made herein will be understood to likewise apply to other forms of the invention.

One example system of the method is a collection device having a flow through micro scale plate arranged to collect analyte and deliver a concentrated pulse of analyte to a detector system upon demand through heating. Analyte fluid flow is passed over or through at least one sorbent plate, which may include passages to pass analyte fluid flow, for example analyte vapor. Some embodiments of the invention use a series of two or more flow through micro scale plates. In some example embodiments, micro scale plates include a sorbent coating and holes for analyte fluid flow through the plates. After a period of collection, analyte may be provided to a detector system from the plate by heating the plate. Example embodiment plates include an integrated heater trace.

Figure 1:
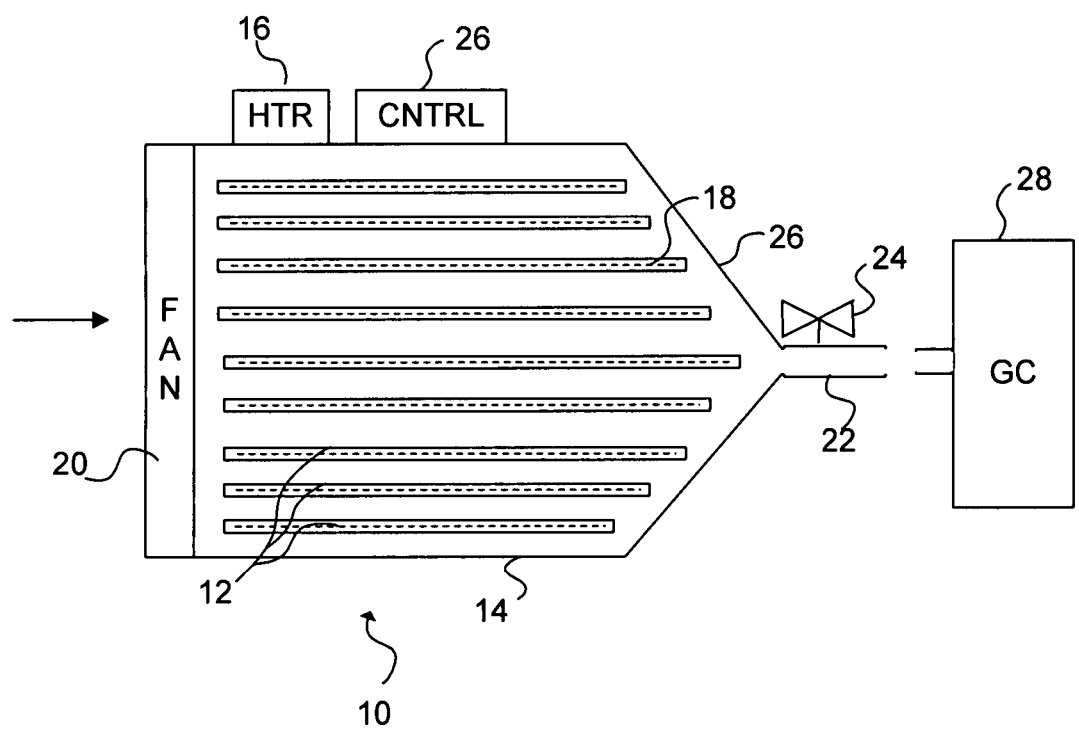
FIG. 1 is schematic of an example collection device of the invention.

FIG. 1 is a schematic illustration of one suitable collection device or pre-concentrator 10 of the invention. FIG. 1 is schematic only, and has not been drawn to scale. The device 10 system includes an array of sorbent coated flow-through plates 12 enclosed in a housing 14. The term "plates" is intended to be interpreted broadly as used in this context, and may include any structure useful for collecting analyte, with examples including the walls of a housing, tube, passage, or the like. The plates 12 may be arranged in any of a number of manners, with an example being the stacked configuration of FIG. 1. The plates 12 are configured to allow for fluid flow thereover within the housing 14. Any number of plates 12 may be provided, with examples being from 1 to a multiplicity. The housing 14 may be constructed of any suitable material, with metals and polymers being examples. The material used should be suitable to withstand temperature, pressure and corrosive characteristics of applications.

The plates 12 may be made of conductors such as metals, semi-conductors such as silicon based materials, or dielectrics. In micro scale applications, the material for the plates 12 should be suitable to micro fabrication processing. This includes semiconductors and dielectrics. Silicon semiconductors are suitable, as are Group III-V materials. Some example dielectrics include ceramics, glass, polymers, crystalline quartz, fused silica, resins, etc. Silicon carbide is another example material, and would be suitable for high temperature applications.

The plates 12 may include a sorbent coating thereon (on one or both surfaces) for collecting the analyte. The plates 12 may include multiple sorbent coatings. It will be appreciated that use of the term "a sorbent coating" is therefore not limited to a single sorbent coating. Such a coating, however, is not necessary in all invention embodiments. A plate may include a metal mesh structure that does not use a sorbent coating, for instance, that is suitable to collect analyte. Sorbent coatings may be provided in varying thicknesses selected based on the application, the sorbent used, and other design considerations. Use of different sorbent materials for example, may be useful to target different agents and toxic industrial chemicals.

Desorption is by heating. In the case of multiple types of sorbent, there can be a thermal desorption sequence constructed based upon desorbing temperatures. Various examples of sorbent materials may include micro porous materials, sol-gel oxides and polymers. Example sorbent coatings include sorbent polymer(s) that act to selectively collect and concentrate analyte at ambient temperatures. Functionalized polycarbosilanes have been used as sorbent coatings. Other examples include chemoselective polymer films, various forms of carbon including carbon nanotubes, nanostructured ceramic or polymer particles and films, composite materials, block copolymers, combinations thereof, and like materials. Artisans will find guidance for selecting appropriate sorbent materials in "Choosing Polymer Coatings for Chemical Sensors," McGill, R. A.; Abraham, M. H.; Grate, J. W. CHEMTECH 24, 9 (1994) p. 27-37. Example sorbent coatings will have high temperature stabilities, which are necessary for thermal cycling.

Sorbent coatings may be applied by a number of techniques, and the particular application method may depend upon the type of sorbent coating. Dip coating is one technique. A flow through plate is prepared for bonding of the sorbent, which may involve cleaning and drying, for example. It is then dipped into a solution of the sorbent coating. Other techniques include, for example, aerosolized coating, syringe coating, inkjet coating, laser evaporation, spin coating and washing sorbent solution over a flow through plate.

The plates 12 may have a minimal thickness necessary for fabrication processing and for structural integrity during assembly and use. The plates 12 must withstand contemplated fluid flows, and the stresses induced by the fluid flow variations and temperature fluctuations introduced during the collection and desorption of analyte. Plates of the invention may be made very small, both in width and thickness. An example plate may have a 1-10 mm width, for example, and may have a thickness from a few micrometers to hundreds of micrometers or more. Small thicknesses are generally preferred to provide a low thermal mass and corresponding rapid heating and desorption. Any of a number of simple or complex plate geometric shapes may be used.

Collection devices of the invention include multiple analyte embodiments. Using more than one sorbent in different sections of flow-through plates, either on a single plate or on multiple plates, allows a device of the invention to collect more than one type of analyte. In one embodiment, a single plate, which may or may not be part of a series of plates, includes multiple sorbent sections. In another embodiment, plates in a series of plates each include a single sorbent while the series of plates provides multiple sorbents by having at least one plate coated with a different sorbent than other plates in the series of plates.

A heater is provided for heating the plates. A heater power supply 16 is provided and linked to a heater for heating the plates 12. In the system 10, the heater comprises individual heater traces 18 in (or on) each of the plates 12 (illustrated as dashed lines in FIG. 1). The traces 18 may be arranged on the surface of the plates 12, for example, placed in slots (not illustrated) in the plates 12, or embedded within the body of the plates 12. The heaters traces 18 may be lengths of conductive material forming a resistive heating element. Use of separate heater traces 18 allows desorption to be zoned. That is, the heater traces 18 may be individually controllable to form separate heating zones on one or more of the plates 12. This is useful, for example, in embodiments of the invention that use different sorbents in different zones. It is also useful in embodiments of the invention where it is desirable to be conducting collection in one zone, while conducting desorption in another zone.

The heater traces 18 may be formed of conductive materials having a suitable resistance. Generally, materials that are preferable for heater traces are materials having a high temperature coefficient of resistance, minimal susceptibility to oxidation and low thermal conductivity. Platinum, gold, and copper are some, but not all, examples. In one example, micro-scale Pt strips deposited on the plates 12 are used. Other example materials include all materials that are amenable to micro fabrication processing, and suitable for the conditions of operation.

Other heating mechanisms may also be used in embodiments of the invention, including, for example, radiation induced heating or heating by conduction or convection mechanisms. However, the resistive trace 18 is one example element that has been found to provide desirably fast heating rates to deliver a concentrated pulse. If another heating mechanism is used, it may be configured to produce the rapid desorption effect. The power supply 16 may be any suitable electric power supply, with examples including DC batteries and AC. One example includes a 30 V DC supply 16. Power supply 16 voltage and heater 18 resistance may be varied as desired to cause heating at a suitable rate. An in-line resistor (not illustrated) or like mechanism may be provided to control amperage.

A fan 20 covers an inlet to the housing 14 and directs fluid flow in the direction shown by the arrow of FIG. 1 from the environment into the housing 14. Although only one fan 20 is illustrated, a plurality may be provided. The fan 20 may have an open and closed position, with fluid flow prevented in the closed position. Opposite the fan 20 the housing 14 includes a narrowed exit port 22 fitted with a valve 24 for opening and closing the port 22. The port 22 may be dimensioned as desired for particular applications, and can be configured to be received by a testing device such as a gas chromatography system. The housing 14 may include a narrowed portion 26 leading to the port 22 to concentrate and direct fluid flow.

In operation, the fan 20 is opened and turned on to direct fluid (such as a gas including an analyte of interest) into the system housing 14 and over the plates 12. The exit port 20 is opened to allow flow through. Analyte accordingly contacts the sorbent on the plates 12 and is adsorbed thereon. After some period, the fan 20 is turned off and closed. The valve 24 may likewise be closed to isolate the housing 14 interior, although in some applications it is not necessary to isolate the interior as the analyte is held by the sorbent on the plates 12. The internal walls of the housing 14 should be inert to the analyte of interest, either because of material properties or by active heating of the internal surface to avoid sorption.

A controller 26 controls the fan 20 and may also be linked to the valve 24 and the heater 16. The controller 26 can be a processor based device (with one example being a personal computer) that includes a memory and program instructions for controlling various elements, such as one or more of the fan 20, valve 24 and heater 16. Although the controller 26 has been illustrated as a single device, it may be provided as several individual controllers 26 that collectively control the fan 20, valve 24 and heater 16. Some or all of these devices, for example, can be provided with an internal controller.

In other example systems of the invention, no fan 20 is provided. These other systems exploit inherent environmental circulation to draw fluid containing analyte into the housing and into contact with the plates. Or, in some micro or mini scale invention embodiments, a housing may be pre-evacuated to a pressure below atmospheric and sealed. Once in the field, the seal may be removed to expose the housing interior to the environment and thereby draw environmental fluid (such as air) into the housing.

Referring again to the example system 10, following collection and concentration, the housing port 22 may be connected to a detector system 28 such as a gas chromatography system. The controller 26 may open the valve 24 and power the heater 16 to a level sufficient to cause the plates 12 to reach a desorbing temperature sufficient to cause the analyte to be released. The fan 20 may optionally be engaged to cause fluid flow into the testing system 28, although in many applications this is unnecessary.

The physical configuration of the housing 14 and/or the detector system 28 may be highly compact for a self-contained field analysis device—the detector system 28 may be integral with the housing 14. In other embodiments, including that schematically shown in FIG. 1, the housing 14 is detachable from the detector system 28. This is advantageous for some applications where portability is desirable. The housing 14 might include a carrier aid, such as a handle or clip. The overall dimensions of the system 10 may be such that the housing may be conveniently carried on the body of a person. Embodiments of the invention include both modular collection devices and stand alone analysis devices having a collection device and a detector system, e.g., a transducer, control circuitry, microprocessor, memory, pneumatic fluidics, a manifold and the like.

Both modular collection devices and stand alone analysis devices of the invention may be highly compact. An example modular collection device unit can be made small enough, for example, to be conveniently worn on a person, affixed to a vehicle, inserted into the process flow of a machine in a production line, attached to plant life, portions of buildings, in ventilation systems, on cargo, on baggage, in baggage screening areas, etc. For example, a modular collection device of the invention might be clipped to a belt or clothing, or attached to clothing by a hook and loop fastener, e.g., Velcro®. In a method of use, such a device may be carried in an environment by a person to collect sample, and then attached to a detector system after a period of collection.

Also, a system of the invention may include a mini or micro scale detector system for a highly compact and complete micro analytical device of the invention. An example system includes a chemresistor detector system in a MEMS integration with a collection device including flow through micro scale sorbent plates, a micro GC column, a power source, and electronics. The micro scale sorbent plates of the invention permit very low pressure drops, and enable, for example, the use of inexpensive low power fans of the type used in lap top computers to generate high collection flow rates with very low power consumption. Embodiments of the invention meet important design constraints imposed by considerations necessary for realization of practical self-contained portable micro analytical devices. These constraints include minimal power consumption for collection and desorption processes, high fluid flow, a small physical footprint, and a robust mechanical design.

In the system 10, the controller 26 is configured to cause the heater 16 to heat the plates 12 to a temperature, and to measure a property of the plates 12 at this temperature in order to determine one or more of the amount of analyte on the plates 12 or whether a contaminant is present on the plates 12. The property measured may include, for example, a thermal property of the plate measured through an electrical property of the heater traces 18. These features of the system 10 of the invention may be best illustrated through discussion of methods of the invention presented below.

As discussed above, when using collecting devices including discussed here and others of the type that include plates with sorbent thereon for storing analyte, it can be difficult to determine the amount of analyte collected, and/or to determine that sufficient, maximal and/or an optimal amount of analyte has been collected for testing. Taking a mass difference comparing the loaded collection device and the pre-loading empty device may not be practical due to the difficulties associated with detecting what is often a micro-scale mass difference. Another unresolved problem in the art relates to the ability to detect non-volatile and other contaminants that accumulate over time on the sorbent. Dust and other non-volatile particulate may over time contaminate the sorbent and begin to lower efficiencies of the sorbent as active sites become clogged by the contaminants and as other contaminating effects occur. Determining when contaminants are present and in what quantity, however, is difficult. Such determinations generally face the same problems as do determination of the amount of analyte that has been collected.

Figure 2:
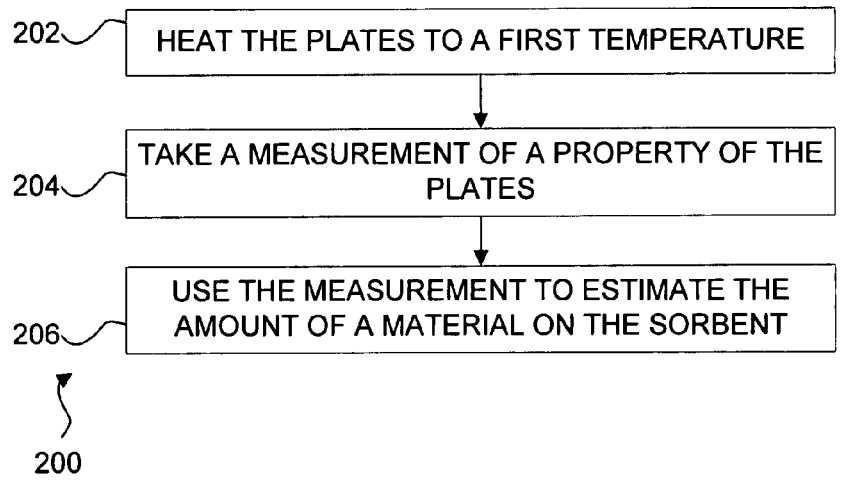
FIG. 2 is a flowchart illustrating one example method of the invention.

Example methods and systems of the invention are useful to address these and other problems in the art. In particular, some example methods and systems of the invention are directed to determining an amount of material on the sorbent, where the material may be collected analyte or contaminants. FIG. 2 is a flowchart illustrating one such example method of the invention. The method 200 is for operating a collection device, which can be, for example, a collection device such as the device 10 of FIG. 1, or any collection or preconcentrator device that includes plates for collecting analyte that is released when the plates are heated to a desorbing temperature. In description of the method of FIG. 2, reference may be made for illustration to elements of the system 10 of FIG. 1.

In a first step of the method, the plates 12 are heated. Block 202. Heating the plates 12 may be accomplished, for example, using a heater 16 and heater traces 18. Other heaters may also be used, including convective and radiative heaters. The temperature that the plates 12 are heated to may be greater or less than the desorption temperature. If the task at hand is to determine the amount of analyte material collected prior to testing, the temperature will be less than the desorption temperature. If, on the other hand, the task at hand is to determine whether contaminant is present, the temperature may be (but is not necessarily) greater than the desorption temperature.

The method of FIG. 2 further includes a step of taking a measurement of a property of the plate 12. Block 204. The property may be one or more of a thermal property or an electrical property of the plate 12, with one example being the transient thermal constant of the plate 12. Other properties are contemplated. This step may be taken after heating the plate 12 to the elevated temperature (Block 202), may be performed during the step of heating the plate 12 (i.e., at the same time as Block 202), or may be performed at both during and after heating. That is, the step of taking a measurement of a property of the plate is done at one or more of during the step of heating the plate and after the plate has been heated to the elevated temperature.

Finally, the measurement is used to estimate the amount of a material on the sorbent coating on at least a portion of the plate 12. Block 206. As will be discussed below this step may include, for example, estimating an amount of analyte on the sorbent based on the different thermal or electrical properties of the plate as compared to the same properties of the plate when no sorbent is present. Having now presented one example embodiment system 10 and method 200 of the invention, more detailed embodiments may be illustrated.

Figure 3:
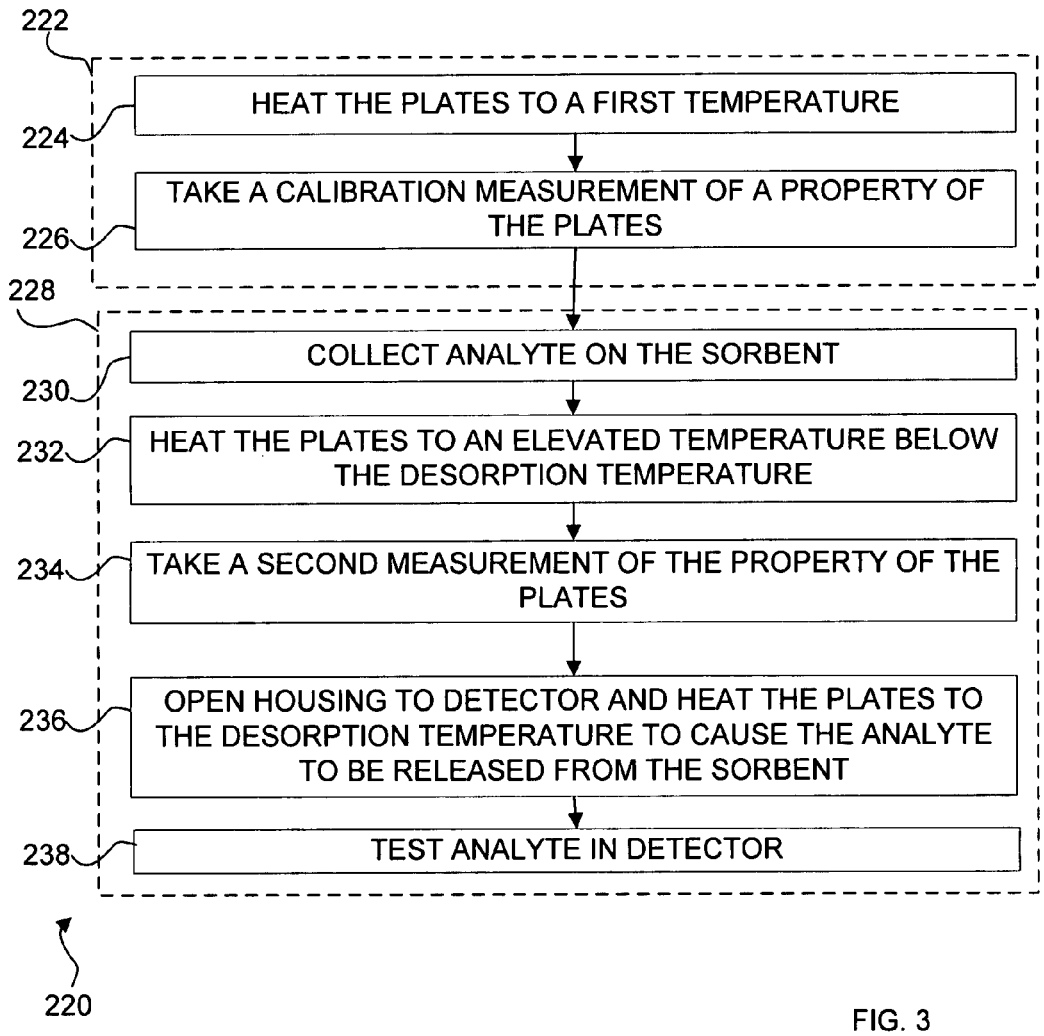
FIG. 3 is a flowchart illustrating an additional example method of the invention.

FIG. 3 illustrates one such example embodiment 220. The method of FIG. 3 is useful to estimate the quantity of analyte contained in the collection device. In addition to the general steps of FIG. 2, the method of FIG. 3 includes performing an initial calibration. Example steps of calibration are contained in the dashed line box 222, and may collectively be referred to as "calibration" for convenience. These steps include initially heating the plates to a temperature above ambient. Block 224. This step is performed with substantially no analyte present on the sorbent. This may be done, for example, before any collection has begun. In some invention embodiments, this step is performed when the plates are new or immediately after cleaning so that no contaminants are yet on the sorbent.

The temperature may be any suitable temperature, with greater temperatures generally favored over lower temperatures. In some example embodiments, the temperature is at least about 10° C. above ambient. In others it is higher, and in some cases much higher. Higher temperatures are believed to generally yield more meaningful results. Benefits of higher temperatures must be balanced, however, against increased energy and time required to reach those temperatures. Temperatures of about 50° C., 75° C., 100° C., 150° C., 200° C., and others may be useful in different methods of the invention.

In an additional step, a calibration measurement of one or more properties of the plates is taken. Block 226. This may be performed after the plate has been heated to the elevated temperature, or may be performed during heating. Any of a number of different properties may be measured, with examples including thermal and electrical properties. Some particular examples include plate temperature, plate electrical resistance, and plate conductivity (thermal or electrical). In some example methods of the invention, the property is transient, which as used herein is intended to be broadly interpreted as being measured over time. As an example, the plate's change in temperature over time as the plate cools after reaching the temperature may be taken.

In one example embodiment, the step of taking a calibration measurement includes determining the thermal constant of the plates. Those knowledgeable in the art will appreciate that the thermal time constant $T_1$ may be determined by measuring temperature versus time T for a material as it cools or as it is heated, using the relationship:

$$y = A \times \exp\left(\frac{-T}{T_1}\right) + y_0$$

where y = temperature of the at least one plate, and A and $y_0$ are constants. In some invention embodiments, temperature of the plates is determined through measuring electrical resistance—which is directly proportional to temperature. As the temperature of the plates, which may be made of a metal, semiconductor, or dielectric, changes, so does its resistance. By measuring the plate temperature directly (or indirectly through measurement of some related property such as electrical resistance) over time, $T_1$ can be determined. In addition to the plate, some portion of it may be measured with an example being a heater trace on it.

Figure 4:
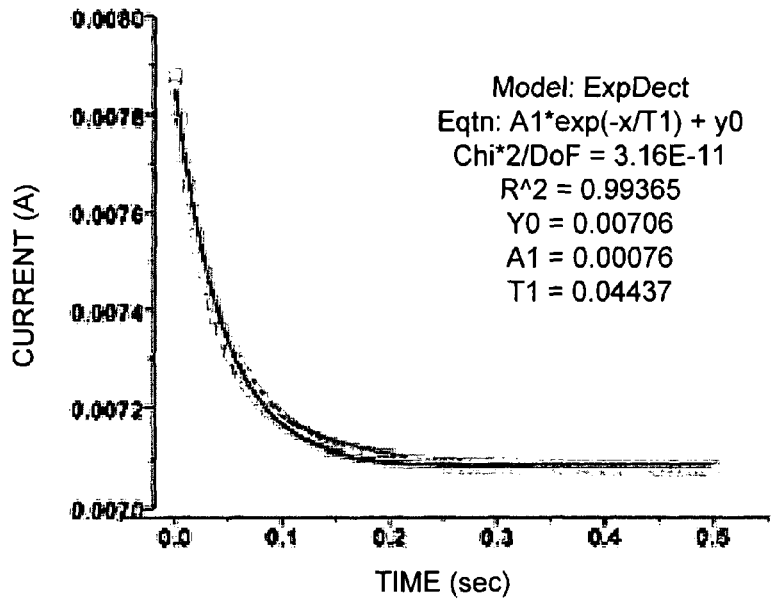
FIG. 4 is a data plot useful to illustrate an example embodiment of the invention.

The chart of FIG. 4 illustrates one example determination. The current traveling through the plate resultant from a constant voltage is plotted along the vertical axis. Because the voltage is constant, this current varies directly with resistance of the plate according to the relationship: voltage=I×R; where I is current and R is resistance. Time is plotted along the horizontal axis. The constants A and $y_0$ can be empirically determined through the plot, as can be the thermal constant $T_1$. Temperature of the plates may be measured using a suitable sensor such as a thermocouple. In many applications, including micro-scale ones, it is often more convenient to measure temperature through measurement of the resistance of the plates or the heater traces on the plates. One example step includes determining temperature by measuring current traveling through the heater traces and therefore resistance while at constant potential.

Figure 5:
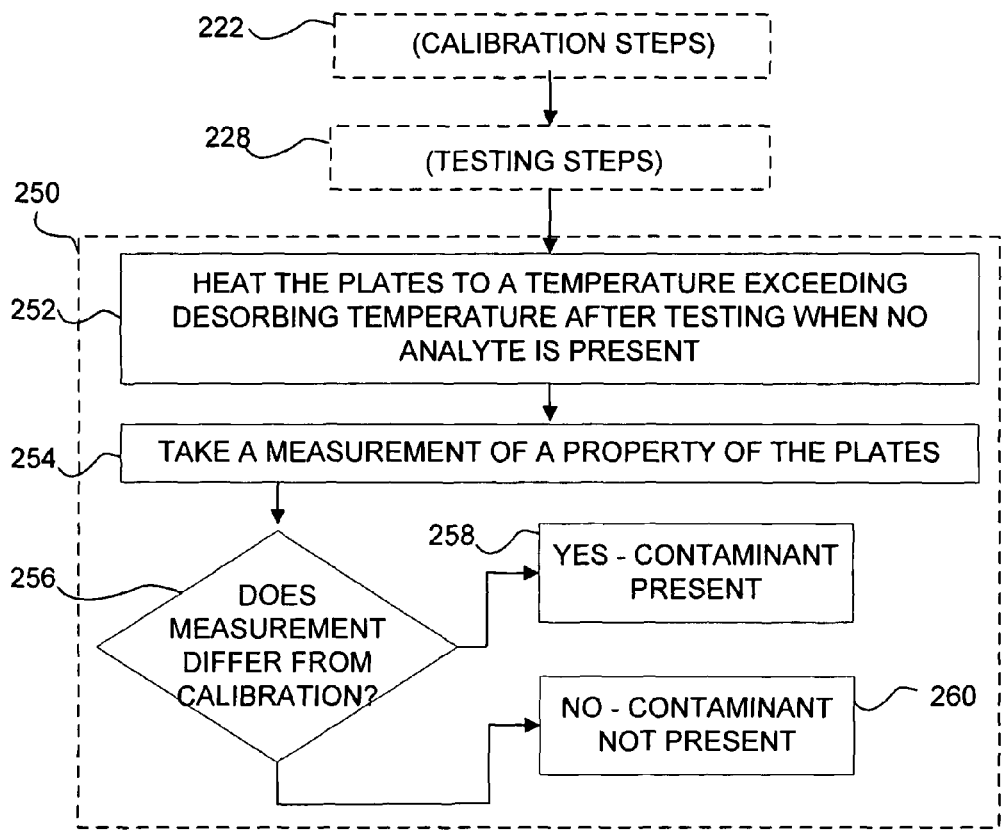
FIG. 5 is a data plot useful to illustrate an example embodiment of the invention.

The chart of FIG. 5 illustrates a second example determination. In this chart, time verses temperature for a plate has been plotted. A constant voltage has been applied to heat the plate. Again, the constants A and $y_0$ can be empirically determined through the plot, as can be the thermal constant $T_1$. Other determinations can likewise be made using this or other thermal or electrical data.

Referring once again to the method of FIG. 3, steps of performing a test are next practiced. Steps of testing have been grouped in the dashed line Box 228 and may collectively be referred to as "performing a test" or "testing" for convenience. It will be appreciated that these steps need not necessarily be performed immediately after performing a calibration, or for that matter within any particular time period after performing a calibration (although they could be).

In a first step of performing a test, an analyte is collected on the plate or sorbent. Block 230. This step may include, for example, causing a fluid to flow past the plates and sorbent thereon using a fan or the like. After a sufficient time period (which will vary with particular application), the collection device housing that contains the plates (e.g., housing 14 of FIG. 1) is closed to isolate its interior. This step of isolating the housing interior may not be necessary or included in some other method embodiments, since the analyte will be retained by the sorbent regardless of fluid movement through the housing interior.

In some applications, however, it will be desirable to isolate the housing interior to ensure that further collection on the sorbent does not occur. If, for example, a sample is desired from a particular room or geographic location, the sample can be collected at that location and the housing then isolated or closed. This helps ensure that any analyte collected originated from the desired location and not during later transport or storage.

Following collection, the plates are then heated to a temperature above ambient but below the desorbing temperature of the analyte. Block 232. The temperature may be, but need not be, the same as the temperature that the plates were heated to during calibration. Higher temperatures are generally preferred over lower ones. Selection of a particular temperature to heat to should balance the general benefits of accuracy afforded by higher temperatures against the advantages of shorter required time periods and smaller input energy of lower temperatures.

The temperature that the plates are heated to in step 232 should be below, and preferably significantly below, the desorbing temperature. This avoids causing the analyte to be released from the sorbent during this step. The difference between this temperature and the desorbing temperature may be selected as desired. Depending on the physical configuration of the plates, heater traces, and temperature measurement means, there may be some risk that there are local "hot spots" on the plates that have a higher temperature than that being measured for the plate. Getting too close to the desorption temperature risks that one or more localized "hot spots" on the plates may reach the desorption temperature and cause some analyte to be released. In many applications it is believed that it is useful to set this temperature at least about 10° C. below the desorbing temperature, and at least about 25° C. below the desorbing temperature in other applications.

After the plate has reached its desired temperature, a measurement is taken of a property of the plate. Block 234. The property may be, but is not necessarily, the same as that measured during the calibration of Block 222. It may be, for example, a thermal or electrical property of the plate such as a transient temperature or resistance measurement. In some applications, the measured property will be the thermal constant $T_1$ of the plate determined by measuring the temperature change over time after or while heating to the desired temperature, as discussed above with reference to FIGS. 4 and 5.

This new thermal constant $T_1$ determined through the step of Block 234 will differ from that determined during calibration due to the presence of the analyte on the sorbent. The presence of this material changes the thermal behavior of the plates. The change is evidenced by its characteristic cooling or heating over time and hence its thermal constant $T_1$. A difference between the $T_1$ determined during calibration 222 and the $T_1$ determined during testing 228 therefore is a monotonically increasing function of the amount of analyte material collected and stored on the plates.

The units of $T_1$ are seconds. Directly converting the difference between the calibration $T_1$ and the testing $T_1$ to a mass of analyte present can be performed though an accurate determination will depend on the thermal properties of the collected material. Also, if some property other than $T_1$ is measured, the conversion to units of mass may be more straightforward. Use of a computer or other processor based device to perform this conversion may be helpful.

As an alternative to performing these calculations, it has been discovered that qualitative determinations can be achieved through developing a history through use. Doing so can eliminate the need for the calibration steps of Box 222. (or, put another way, steps of calibration may be thought of as pervious steps of measurement during pervious tests). Accordingly, in some invention embodiments the calibration steps 222 are eliminated. In these invention embodiments, steps of storing the property (such as $T_1$ or another thermal or electrical property) calculated at Block 234 during multiple test runs is performed together with resultant test results. Over time, this data can be used to perform steps of developing a collection of data or knowledge base that yields a threshold "pass-fail" property value that indicates whether sufficient analyte has been collected to proceed with testing.

As used herein, the term "knowledge base" is intended to be broadly interpreted as a collection of data useful to inform a decision and/or to form an inference, estimate, or conclusion. Knowledge bases may be further understood through consideration of their use in some embodiments of the invention. For example, multiple test runs and corresponding measurements of a property through the step of Block 234 might suggest that a property value of z or greater corresponded to sufficient analyte having been collected, but property values of less than z indicated insufficient analyte was present.

If sufficient analyte has been collected for testing, the desorption path is then opened to the detector system and the plates are heated to the desorption temperature to cause the analyte to be released from the sorbent. Block 236. A step of opening the desorption path has been summarized in Block 236 as opening the housing. It will be appreciated that this is intended to be broadly interpreted as allowing the analyte to be released. This step is not necessary if the housing has not been isolated.

These steps may be performed immediately after Block 236, or may be performed at some later time. If insufficient analyte had been collected, further collection can be performed until the measured property determined at Block 234 indicates that sufficient analyte has been collected. The detector system may be any desired detector including those discussed and described above, including an IMS detector, a GC detector, a spectrometer, and the like. As discussed above, a fan, vacuum pump or the like may be operated to induce flow into the detector, or convective flow may be relied on to transfer the vaporized analyte from the collection housing to the detector.

The analyte is then tested in the detector system. Block 238. In methods of the invention that include steps of storing test results to build a collection of data or knowledge base, these results may be stored. The results stored may be an indication of whether sufficient analyte was present to perform a test. Other results may also be stored.

Figure 6:
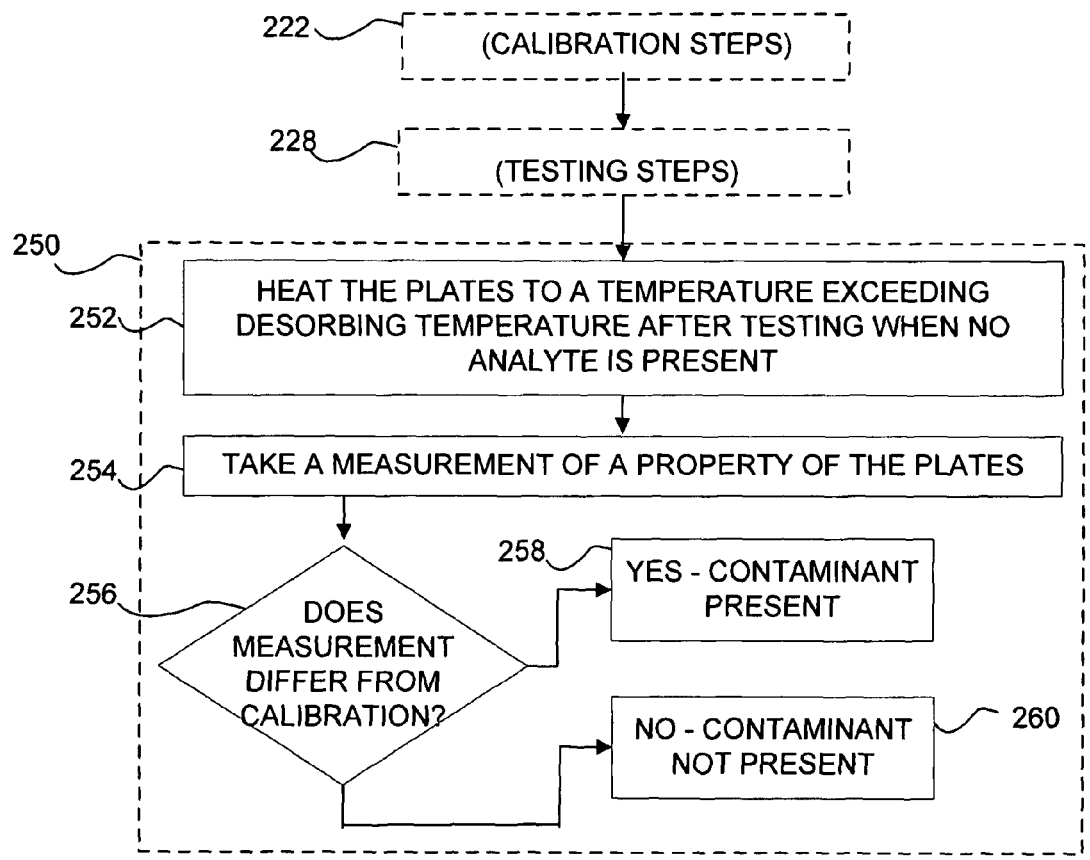
FIG. 6 is a flowchart illustrating an additional example method of the invention; and, FIG. 7 is a schematic of an example system of the invention.

FIG. 6 illustrates still an additional method of the invention. This example method is directed to determining whether or not contaminant is present on the sorbent, and if so in what quantity. The method begins with performing a calibration as described above with reference to the steps of Box 222 of FIG. 3. A test is then run according the steps of Box 228 described above with reference to FIG. 3. In some invention embodiments, the steps of Box 228 might be altered within the method of FIG. 6 by omitting the step of Blocks 232-234. That is, the method of FIG. 6 does not necessarily require estimating the amount of analyte collected as part of performing a test.

Following the performance of one or more tests, the method of FIG. 6 proceeds to perform a set of steps useful to determine whether contaminant is present on the sorbent, and if so to provide an estimate of what quantity. These steps are contained within dashed line box 250, and may collectively be referred to as "contaminant determination" for convenience.

These steps begin with heating the plates to a temperature greater than the desorbing temperature. Block 252. Selecting a temperature greater than the desorbing temperature should ensure that all analyte (as well as all other volatile materials having a boiling point below the selected temperature) are removed from the sorbent. Other invention embodiments, however, may use temperatures that are below the desorbing temperature so long as no analyte is present. Temperatures greater than the desorbing temperature are preferred, however, to ensure that analyte is not present.

A measurement of a property of the plates is taken. Block 254. This may be performed after the plate has been heated to the desired temperature, or during the heating. This may include, for example, measuring a thermal or electrical property. One particular example is determination of the plates' thermal constant $T_1$ through measurement of the plate's temperature over time as it cools or is heated, and as described herein above with reference to the steps of Blocks 222, 228 and FIG. 4. Other example embodiments may measure other properties as an alternative or in addition to the thermal constant.

The $T_1$ (or other property) measured during the steps of contaminant determination (Block 250) is then compared to the $T_1$ (or other property) measured during the steps of calibration (Block 222). Since no analyte was present during the calibration steps of Block 222 and none is present during the steps of contamination detection of Block 250, the two values should be substantially the same. If so, a determination that no contaminant is present is made. Block 258. Any significant difference between the values indicates a change in the physical property of the plates since calibration. In the method of FIG. 6 this is indicative of the presence of a non-volatile contaminant, with examples including dust particulate and the like. Block 260. It is noted that some minimal difference may be due to limitations in accuracy of measurement, changing ambient conditions during calibration verses testing, and the like. Accordingly, some minimum difference may be required to conclude that contaminant is present. The amount of the required minimum difference may be determined through calculation, empirical testing, or other methods.

The amount of contaminant present may be determined through calculation using the different property values (such as $T_1$) determined during calibration and testing. Or, in other invention embodiments, a knowledge base may be built over time that attempts to identify a pass/fail threshold for the measured property. For example, it may be that some minimal amount of contamination does not have a noticeable effect on testing. Multiple test run results may indicate that after a certain value has been reached through the contamination determination steps of Block 250, however, contamination has occurred to an extent that cleaning or reconditioning should be performed.

Many variations of particular steps of the methods of FIGS. 2, 3 and 6 may be practiced. For example, these methods have generally included heating the plates to a particular elevated temperature, and then measuring a thermal or electrical property of the plate. Changes in these properties are generally indicative of changes of the analyte (and/or contaminant) loading on the plates. In other invention embodiments, however, one or more properties of the plates may be measured during the heating of the plates. In one particular example, the amount of power required to cause the plate temperature to increase a particular amount (and/or at a particular rate) may be useful to measure a property of the plates. Many different variations of these steps may be practiced that generally include taking some measurement of some property of the plates (including the sorbent thereon) as the temperature or power supplied to the plates changes. Many particular examples include steps that measure some thermal and/or electrical property.

Methods of the invention may also be practiced on collector systems such as the device that includes multiple heater zones. A method of the invention may include controlling each of the zones independently of one another. Put another way, a method of the invention may include practicing a method such as that illustrated by any of FIGS. 2, 3 or 5 on one or more individual heater zones in a collection device that includes multiple zones. This may be useful, for example, to pinpoint the location of contamination to one particular zone, to determine the loading of a particular zone, or for other reasons. The controller in such a system may be configured to cause a method of the invention to be performed on one or more selected of the plurality of zones.

Some variations of steps of the methods of FIGS. 2, 3 and 6 may be particularly well suited for practice with a device that includes a plurality of individual heater zones. For example, the steps of Blocks 226, 234 and 254 of FIGS. 3 and 5 may comprise heating only one individual zone of the plate, and taking a measurement in an adjacent (unheated) zone. The temperature in the adjacent zone is directly proportional to the thermal conductivity of the plate. The temperature in the adjacent zone may be measured, for example, through measurement of the resistance of the heater element in that zone. Changes in the thermal conductivity indicate a change in the loading (analyte or contaminant) of the plate.

Also, it will be understood that methods of the invention may be carried out by a controller such as the controller 26 of FIG. 1. The controller may also be a controller chip or microcontroller. A controller may be an electrical device, a processor based device such as a computer, a circuit or micro-circuit (which may be embedded on a circuit card or micro-chip) configured to carry out a method of the invention. In many example embodiments of devices of the invention, the device is of a micro-scale, and the controller is in the form of a micro-circuit on a chip included with the device.

Those knowledgeable in the art appreciate that methods of the system also lend themselves well to practice in the form of software programs. Accordingly, an additional method of the invention is directed to a software program including computer readable instructions that when executed by a computer cause the computer to carry out a method of the invention as described herein, including but not limited to the methods described in the flowcharts of FIGS. 2, 3 and 5. It will therefore be appreciated that when discussing a method of the invention herein, description of a computer software program product is likewise being made.

A software program of the invention may be stored in a memory, and may produce output that is likewise stored in a memory and/or is displayed on a display. Example output of different software program products of the invention include a measured property of a plate (such as $T_1$), an estimated amount of analyte or contaminant held on the sorbent, or a pass/fail indication for proceeding with testing.

Figure 7:
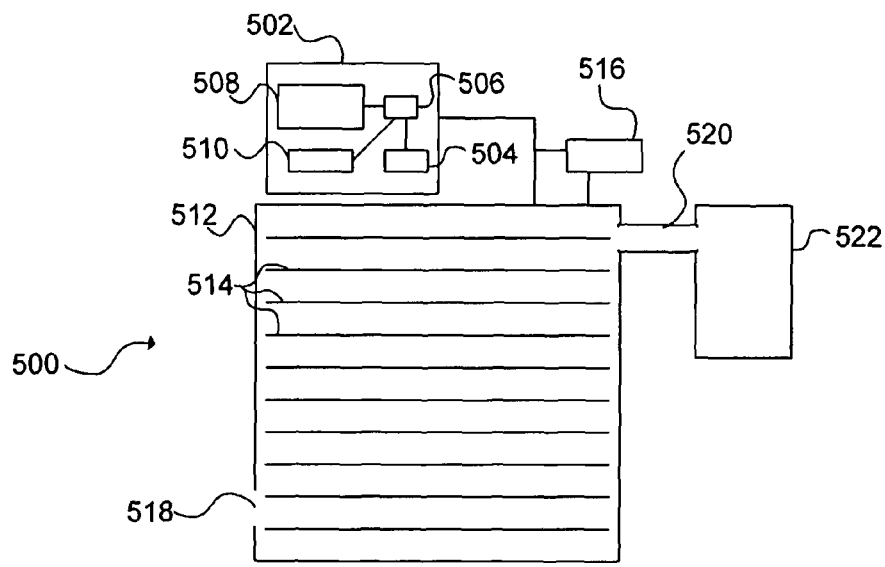

By way of illustration, FIG. 7 schematically illustrates a system 500 of the invention that may be, for example, a collector device or a preconcentrator. The device includes a controller 502 of the invention that is running a software program of the invention useful to cause a method of the invention to be practiced on the device 500. The controller 502 includes a memory 504, a processor 506 and a display 508. The memory may be a magnetic, optical, charge storing, or other memory medium as are known and useful to store digital or analog data. The processor 506 may be an electrical circuit or circuit logic embodied in a circuit, including a microchip, useful to carry out instructions. The display 508 may be any medium useful to display data, with an example being a screen for displaying text and/or numerical input or output data, lights or other indicators for indicating data or device conditions or status, or the like. Data input means 510 may also be provided, with an example being switches, keypads, buttons, a keyboard, or the like.

The device 500 further includes a collection housing 512 that has a plurality of plates 514 contained therein. The plates have a sorbent coating over at least a portion of their surfaces for collecting analyte. The plates 514 also include a heater trace covering at least a portion of their surfaces for heating them to a desired temperature and further include means for determining their temperature. Example temperature detection means include thermocouples, infrared temperature detection devices, and the heater traces which can be used to indicate temperature through measurement of electrical resistance. A heater power supply 516 is linked to the controller 502 and to the collection chamber 512 for heating the plates to a desired temperature. The collection housing 512 includes at least a first port 518 where analyte can enter the housing 512 and at least one exit port 520. The exit port 520 communicates with a testing device 522, which may be for example a GC, spectrometer, other chemical analysis device, or other testing device.

The controller 502 is configured to carry out a method of the invention, with examples including the methods illustrated and discussed with reference to FIGS. 2, 3 and 6. A software program of the invention may be stored in the memory 504 or may be embodied in the circuitry of the processor 506, for example. In carrying out a method of the invention, for example, the controller 500 may carry out a calibration step by heating the plates 514 to a first temperature and measuring a property of the plate (either during their heating or after they have reached the first temperature). A property of the plates may thereby be determined, with an example being their thermal constant. Each of the plurality of plates 514 may be treated individually in these steps, some overall average may be obtained, or some sampling of only a selected portion of the plurality may be used.

The controller 500 may further carry out a step after some amount of analyte has been collected and stored on the plates 514 of heating the plates to a second temperature that is below the desorbing temperature, with an example being 90° C. A property of the plates 514 is measured after heating to this second temperature or during the process of heating to this temperature. A comparison of this property to that measured during the calibration can be used to estimate the amount of analyte stored on the plates 514. The processor 504 may be configured to perform calculations, for instance, that relate the difference in measured plate properties to a mass of analyte. Each of the plurality of plates 514 may be treated individually, some average may be obtained, or some sampling of only a selected portion may be used.

In other embodiments of the system 500, the controller 502 may be configured to perform the steps of testing (e.g., Block 228 of FIG. 4) without having previously performed calibration steps (e.g., Block 222 of FIG. 4). Over time a collection of data or knowledge base may be built that can be useful to predict what plate property values indicate sufficient analyte has been collected sufficient for testing by the testing device 522. Steps of building this knowledge base may include, for example, storing measured plate property values and testing results in the memory 506. A table, for example, may be assembled that relates plate property to an indication of whether the testing device 520 subsequently had a sufficient quantity of analyte available to perform a test. After a suitable number of data points have been collected and stored in the memory 504, the processor 504 may create a linear or other relation that predicts a threshold value for the plate property above which the probability is high that a sufficient quantity of analyte has been collected.

Methods, systems and software programs of the invention contemplate using further data to make such predictions more sophisticated. Other data values that may be collected (through entry using data entry means 510, for example) include, but are not limited to, the type of analyte (specific material, type of material, etc.), physical properties of the analyte (molecular weight, boiling point, desorbing temperature), environmental conditions (ambient temperature, pressure, humidity, etc.), type of testing performed (GC, etc.), and the like.

By way of illustration, one (hypothetical) example set of data that is stored by the controller 502 in memory 504 may be summarized in the form of a table such as:

TABLE 1

Example Data

| Test # | Property Value | Analyte | Ambient Temp (° C.) | Ambient Humidity (% RH) | Sufficient Analyte for Test? |
|---|---|---|---|---|---|
| 1 | 1.097 | A | 21° | 50 | Y |
| 2 | 1.040 | A | 23° | 44 | N |
| 3 | 1.460 | A | 24° | 22 | Y |
| 4 | 1.237 | A | 22° | 15 | Y |
| 5 | 1.119 | A | 22° | 80 | Y |
| 6 | 1.008 | B | 23° | 82 | N |
| 7 | 1.043 | B | 21° | 84 | N |
| 8 | 1.067 | B | 22° | 74 | Y |

The controller 502 and/or the computer program product of the invention stored in its memory may be configured to store data such as that summarized in TABLE 1, and may further be configured to determine or calculate from this data a threshold Property value for indicating that sufficient analyte is present for proceeding with testing for each of analytes A and B, which may take into account such factors as ambient temperature and pressure. This may include, performing a linear, non-linear, or other analysis of the data. At least some data (e.g., "Type of Analyte") may be input using entry means 510, and output data may be displayed on the display 508 and/or stored in memory 504. Other data in addition to that illustrated may be measured, calculated and stored. The controller may also be configured to use this data to perform steps of making predictions, estimates or other data processing steps.

The controller 502 may further be configured (through execution of a computer program product of the invention) to perform a method such as that illustrated above in FIG. 6 and directed to determining whether the plates 514 have a contaminant stored thereon, and to estimate the amount of such contaminant. This may include, for example, the controller 502 causing the plates 514 to undergo a calibration as generally discussed above by heating to a first temperature when no analyte is present and measuring a plate property. Following some number of tests, the controller may then cause the plates to be heated to a second temperature following testing when no analyte is stored on the plates 514.

The second temperature may be the same or different than the first temperature, and in many applications will be greater than the desorbing temperature. A property of the plates is then measured (or is measured as the plates are being heated). A comparison of this measured property to that measured during calibration can be useful to estimate whether contaminant (such as a non-volatile contaminant) is present on the plates. The processor 504 may be useful to perform calculations to estimate the amount of contaminant present.

Computer program products of the invention may cause certain data output to be stored in the memory 506 and/or to be displayed on the display 508. The program product may, for example, display on the display 508 whether a sufficient quantity of analyte has been collected to perform a test with the testing device 522. In another example embodiment, the program product may cause output to be displayed on the display 508 that indicates a contaminant is present on the plates 514, and/or to display the estimated quantity of contaminant present.

While specific embodiments of systems, methods and program products of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. A method for operating an analyte collection device of the type that includes one or more plates for storing analyte, a heating element for heating the one or more plates, and a controller having a processor, a memory, and program instructions linked to the heating element, the controller programmed to perform the method steps of:
heating the one or more plates to a first temperature;
taking a measurement of one or more properties of the one or more plates from a detector at one or more of during the step of heating the one or more plates and after the one or more plates have been heated to said first temperature;
using the measurement to estimate the quantity of analyte collected on the one or more plates; and
heating the one or more plates to at least a second temperature that is greater than the first temperature to cause the analyte to be released from the one or more plates.

2. A method for operating an analyte collection device as defined by claim 1
further including the step of storing the analyte on said one or more plates, wherein the controller is further programmed to perform the step of heating said one or more plates to said first temperature after said analyte has been stored on the one or more plates;
wherein said first temperature is at least about 10° C. above ambient.

3. A method for operating an analyte collection device as defined by claim 2 and further including the step of the controller testing the analyte with an analyzer following the step of releasing the analyte.

4. A method for operating an analyte collection device as defined by claim 1, the controller further being programmed to repeat multiple iterations of the steps of heating the one or more plates to a first temperature, taking a measurement of one or more properties of the one or more plates from a detector at one or more of during the step of heating the one or more plates and after the one or more plates have been heated to said first temperature, and using the measurement to estimate the quantity of analyte collected on the one or more plates, to build a knowledge base through said iterations that is useful to predict a value for said measured property that indicates sufficient analyte has been collected for testing.

5. A method for operating an analyte collection device as defined by claim 4, the controller further being programmed to perform the method steps of storing said measured one or more properties, and storing an indication of whether sufficient analyte had been collected for testing during each of said iterations.

6. A method for operating an analyte collection device as defined by claim 2 wherein:
said one or more plates comprises a plurality of plates organized in a stacked configuration, a sorbent covering at least a portion of each of said plates;
wherein the step of storing the analyte on said one or more plates further comprises causing a fluid containing the analyte to flow past said plurality of stacked plates whereby said fluid contacts said sorbent and the analyte is absorbed by said sorbent.

7. A method for operating an analyte collection device as defined by claim 1, the controller further being programmed to perform the method the step of estimating the amount of contaminant on said one or more plates;
wherein said first temperature is higher than a desorbing temperature for the analyte.

8. A method for operating an analyte collection device as defined by claim 1 wherein said measurement comprises a first measurement, the controller further being programmed to perform the preliminary steps of heating said one or more plates to a third temperature, taking a calibration measurement of said one or more properties of said one or more plates from the detector, and comparing said first measurement to said calibration measurement to estimate the quanity of said analyte.

9. A method for operating an analyte collection device as defined by claim 1, the controller further being programmed to perform the method step of measuring the temperature of said one or more plates from the detector as said one or more plates cool from said first temperature.

10. A method for operating an analyte collection device as defined by claim 1, the controller further being programmed to perform the step of taking said measurement while said one or more plates is being heated to said first temperature.

11. A method for operating an analyte collection device as defined by claim 1, wherein the controller is programmed to measure one or more of a thermal property and an electrical property of said one or more plates from the detector.

12. A method for operating an analyte collection device as defined by claim 1, the controller further being programmed to perform the method step of determining the thermal time constant $T_1$ for said one or more plates using the relationship:

$$y = A \times \exp\left(\frac{-T}{T_1}\right) + y_0$$

where: y=temperature of said one or more plates, T is time, and A and $y_0$ are constants.

13. An analyte collection device, the device comprising:
one or more plates;
a heating element for heating said one or more plates;
a detector for detecting one or more properties of said one or more plates; and,
a controller linked to said heating element, said controller including a processor, a memory, and program instructions configuring the controller to heat said heating element to a first temperature and to measure said one or more properties of said at least one or more plates using said detector, and to use said one or more properties to estimate the quantity of analyte collected on said one or more plates, said controller further including program instructions for configuring the controller to heat said at least one or more plates to at least a second temperature that is greater than said first temperature to cause said analyte to be released from said one or more plates.

14. The device of claim 13, wherein said heating element comprises a resistive trace formed on or within said at least one or more plates, wherein said plates each have a sorbent layer thereon and wherein said one or more plates comprises a plurality of plates arranged in a stacked configuration.

15. The device of claim 13, wherein:
said heating element comprises a plurality of resistive traces formed on or within said one or more plates;
said resistive traces divide said one or more plates into a plurality of zones, one of said zones being a collection zone for collecting analyte, and another being a smaller delivery zone for concentrating analyte from the collection zone in a smaller area and delivering analyte to a detector system; and, said controller further including program instructions for configuring the controller to control each of said zones independently from others of said zones.

16. The device of claim 13 wherein said controller further includes program instructions for configuring the controller to:

perform a calibration by heating said one or more plates to an elevated temperature when no analyte is present and to measure at least one calibration property of said one or more plates using said detector; and, heat said one or more plates to a third temperature greater than said second temperature, to measure a second property of said one or more plates using said detector, and to compare said second property to said calibration value to determine if a contaminant is present on said one or more plates.

17. The device of claim 13 wherein said controller further includes program instructions for configuring said controller to store in said memory said measured property together with data indicating whether sufficient material was present to perform a test, and wherein said controller further includes program instructions for configuring said controller to use said stored data to build a knowledge base over multiple tests useful to predict a minimum value for said property that indicates a sufficient quantity of said analyte is present to proceed with testing.

18. A computer program product including computer readable instructions stored on a memory medium, the program product for use with a collector device of the type that includes one or more plates for collecting analyte, a heating element for heating the one or more plates, a detector for detecting one or more properties of the one or more plates, and a controller comprising one or more computers having a processor linked to the heating element, the analyte being released when the collector device heats the plate to a desorbing temperature, wherein said controller is configured to:

cause the one or more plates to be heated to an elevated temperature that is substantially below the desorbing temperature;

measure one or more properties of the one or more plates using the detector;

use the measured one or more properties to estimate the quantity of analyte collected on the one or more plates; and heat the one or more plates to at least a second temperature that is greater than the elevated temperature to cause the analyte to be released from the one or more plates, when the instructions are executed by the one or more computers.

19. A computer program product as defined by claim 18 wherein said controller is further configured to perform a calibration through the steps of:

heating said plates to a first elevated temperature before analyte is stored thereon;

measuring a calibration property of said plates;

storing said calibration property in a memory;

when the instructions are executed, and wherein the instructions when causing the collector device to determine whether sufficient analyte has been collected cause the collector device to compare the measured property to the calibration property.

20. A computer program product as defined by claim 19 wherein said controller is further configured to measure a contamination property of said plates using the detector, and to compare said contamination property to said calibration property to determine if contaminant is present on said plates, when the instructions are executed.

* * * * *